(12) United States Patent
Potter et al.

(10) Patent No.: US 11,869,667 B2
(45) Date of Patent: *Jan. 9, 2024

(54) METHODS, APPARATUSES, AND SYSTEMS FOR GRADIENT DETECTION OF SIGNIFICANT INCIDENTAL DISEASE INDICATORS

(71) Applicant: Optum, Inc., Minnetonka, MN (US)

(72) Inventors: Brian C. Potter, Carlsbad, CA (US); Mark L Morsch, San Diego, CA (US); Emily V. Ho, San Diego, CA (US)

(73) Assignee: Optum, Inc., Minnetonka, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/454,497

(22) Filed: Nov. 11, 2021

(65) Prior Publication Data

US 2022/0068493 A1 Mar. 3, 2022

Related U.S. Application Data

(63) Continuation of application No. 15/483,567, filed on Apr. 10, 2017, now Pat. No. 11,195,621.

(Continued)

(51) Int. Cl.
*G16H 50/30* (2018.01)
*G16H 30/20* (2018.01)
(Continued)

(52) U.S. Cl.
CPC .......... *G16H 50/30* (2018.01); *G06F 40/205* (2020.01); *G06F 40/30* (2020.01); *G16H 10/60* (2018.01);
(Continued)

(58) Field of Classification Search
CPC ........ G16H 50/30; G16H 10/60; G16H 15/00; G16H 30/20; G16H 30/40; G16H 50/20;
(Continued)

(56) References Cited

U.S. PATENT DOCUMENTS 6,292,771 B1 9/2001 Haug et al.
6,915,254 B1 7/2005 Heinze et al.
(Continued)

OTHER PUBLICATIONS

Daugherty et al., Tracking Incidental Findings, vol. 15, No. 7 (Jul. 2014). Retrieved from the Internet: <URL: http://www.radiologytody. net/archive/rt0714p6.shtml>. 2 pages.
(Continued)

*Primary Examiner* — Mamon Obeid
*Assistant Examiner* — Alaaeldin M Elshaer
(74) *Attorney, Agent, or Firm* — ALSTON & BIRD LLP

(57) ABSTRACT

Computer program products, methods, systems, apparatus, and computing entities are described for identifying significant incidental findings from medical records. In one example embodiment, an example computing device receives a medical report and derives a textual component from the medical report. The computing device then identifies one or more medical findings from the textual component and determines a clinical context for each of the one or more medical findings. The computing device then identifies one or more clinical cues from the one or more medical findings and generates one or more condition signals from the one or more clinical cues. The computing device then generates a condition alert from the one or more condition signals. The condition alert is indicative of a significant incidental finding. Using various embodiments contemplated herein, significant incidental findings can be identified for follow-up by a user.

17 Claims, 5 Drawing Sheets

Related U.S. Application Data

(60) Provisional application No. 62/319,912, filed on Apr. 8, 2016.

(51) Int. Cl.
  *G16H 15/00* (2018.01)
  *G16H 10/60* (2018.01)
  *G06F 40/30* (2020.01)
  *G06F 40/205* (2020.01)
  *G16H 50/20* (2018.01)

(52) U.S. Cl.
  CPC ............ *G16H 15/00* (2018.01); *G16H 30/20* (2018.01); *G16H 50/20* (2018.01)

(58) Field of Classification Search
  CPC ....... G16H 70/20; G06F 40/205; G06F 40/30; G06F 17/60; G06Q 50/00; G06Q 10/00; G06N 5/02
  USPC .......................................................... 705/2, 3
  See application file for complete search history.

(56) References Cited

U.S. PATENT DOCUMENTS

| | | | |
|---|---|---|---|
| 7,194,483 | B1 | 3/2007 | Mohan et al. |
| 7,379,885 | B1 | 5/2008 | Zakim |
| 7,730,063 | B2 | 6/2010 | Eder |
| 7,908,552 | B2 | 3/2011 | Heinze et al. |
| 8,612,261 | B1 | 12/2013 | Swanson et al. |
| 8,868,436 | B2 | 10/2014 | Gotthardt |
| 9,230,061 | B2 | 1/2016 | Ephrat et al. |
| 10,068,668 | B2 | 9/2018 | Cao et al. |
| 2002/0082868 | A1* | 6/2002 | Pories .................... G16H 10/60 705/3 |
| 2007/0192143 | A1 | 8/2007 | Krishnan et al. |
| 2008/0228530 | A1 | 9/2008 | Bartsch et al. |
| 2008/0228769 | A1 | 9/2008 | Lita et al. |
| 2008/0256329 | A1 | 10/2008 | Heinze et al. |
| 2009/0070140 | A1 | 3/2009 | Morsch et al. |
| 2009/0192822 | A1 | 7/2009 | Regulapati et al. |
| 2010/0145720 | A1* | 6/2010 | Reiner .................... G16Z 99/00 705/2 |
| 2013/0297348 | A1* | 11/2013 | Cardoza ................. G16H 40/20 705/3 |
| 2014/0358585 | A1 | 12/2014 | Reiner |
| 2015/0066539 | A1 | 3/2015 | Sheffer et al. |
| 2015/0310179 | A1 | 10/2015 | Chengat et al. |
| 2016/0019351 | A1 | 1/2016 | Ober, Jr. |
| 2018/0350466 | A1* | 12/2018 | Oliveira ................ G06F 40/205 |

OTHER PUBLICATIONS

International Search Report and Written Opinion for corresponding International Application No. PCT/IB2017/052067, dated Jul. 4, 2017, 12 pages.

Lumbreras, B. et al., Incidental findings in imaging diagnostic tests: a systematic review, The British Journal of Radiology, 83 (2010) 276-289.

Moyle, P. et al., Incidental breast lesions detected on CT: what is their significance? 83 (2010) 233-240.

Munk, M.-D. et al., Frequency and Follow-up of Incidental Findings on Trauma Computed Tomography Scans: Experience at a Level One Trauma Center, The Journal of Emergency Medicine, vol. 38, No. 3 (2010) 346-350.

* cited by examiner

METHODS, APPARATUSES, AND SYSTEMS FOR GRADIENT DETECTION OF SIGNIFICANT INCIDENTAL DISEASE INDICATORS

CROSS-REFERENCE TO RELATED APPLICATIONS

This application is a continuation of U.S. application Ser. No. 15/483,567 filed Apr. 10, 2017, which claims priority to U.S. Provisional Application No. 62/319,912 filed Apr. 8, 2016, the entire contents of which are incorporated herein by reference in their entities.

TECHNOLOGICAL FIELD

Example embodiments of the present invention relate generally to examining and processing medical reports and, more particularly, to methods and apparatuses that utilize gradient detection to identify significant indicators of serious disease incidentally present in clinical reports.

BACKGROUND

The inventors have discovered limitations with existing techniques for identifying diseases that may be reflected in a medical report but that are not the primary reason for creation of the medical report. Through applied effort, ingenuity, and innovation, the inventors have solved many of these identified limitations by developing a solution that is embodied by the present invention and described in detail below.

SUMMARY

As healthcare and diagnostic technologies continue to improve, more and more health-related data is generated in increasingly more detailed and accurate forms. This increasing amount of data can often provide insights into underlying or incidental medical issues, which were not part of the original purpose for the collection of the data. For example, diagnostic exams ordered for one reason, such as a computerized tomography (CT) scan to assess for skeletal and internal injuries following a motor vehicle accident, may reveal evidence of an unrelated disease, such as a cancerous tumor. Identification of these incidental findings can provide healthcare advantages by helping to catch previously undiagnosed diseases and triggering the start of treatment before the condition reaches a more advanced and problematic state.

Examples of medical data where incidental findings can be found is not limited to CT scans. For example, a lung scan could indicate a clogged artery, an x-ray for back pain may show a suspicious spot on the liver, and a cystitis urinalysis could yield trace protein in the liver. Each of these findings can be indicators of serious diseases that require treatment as soon as they are discovered. Indeed, failure to investigate these findings may have significant health and financial consequences, including substantial disability and/or medical cost, risk of medical malpractice claims, and lost opportunities to treat a disease at an early stage.

That said, ancillary findings are frequent in medical exams and although some may be very significant, such as an identification of cancer, not every ancillary finding from a report is an indicator of a serious disease. Often, it takes skill and specific knowledge of a disease and a patient to assess the significance of an ancillary finding and provide an accurate diagnosis. This mixture of insignificant and significant ancillary findings combined with the dependence on human skill and knowledge to distinguish between the two has historically led to inconsistent follow-up and treatment for many serious or significant incidental findings.

Indeed, despite the potential severity of diseases associated with some incidental findings, follow-up by healthcare providers is low. While physicians may desire to follow-up on every ancillary finding in a medical exam, physicians are often required to review many exams per day and thus there are practical limits on the time they can spend on each review. This time limitation can cause small details to be unintentionally overlooked or ignored. These small details may also be overlooked when the report is being drafted, for example incidental findings may be included in the raw data or other sections of the report, but left out of the summary or impressions section. Additionally, a physician may not have enough experience with certain kinds of medical reports to properly identify incidental significant disease factors for a patient or conversely may not have enough familiarity with a patient and the patient's history to properly diagnose a significant incidental finding. For example, a primary physician may be aware of a patient's medical history but may not recognize the significance of an incidental finding, while a radiologist writing a report may not be aware of the potential significance of an incidental finding to the patient due to a lack of familiarity with the patient's history and medical context.

On the other hand, it is important not to over-emphasize or over-report incidental findings that are not significant. Over-reporting of insignificant findings can overwhelm and panic a patient, divert attention away from the primary condition being treated, and lead to unnecessary tests and treatments that add unneeded risks to the patient (e.g. exposure to radiation or radioactive agents, exploratory procedures, etc.). Additionally, a system that highlights every finding from a given exam or report, regardless of whether it relates to the primary condition being treated or is an incidental finding, may cause physicians and patients to ignore the findings of the system, thus frustrating the potential for follow-up on meaningful findings.

The description herein provides a dynamic framework for highly-selective and accurate detection of incidental findings and identification of significant diseases related to those incidental findings. Example embodiments described herein include the use of gradient levels of risk and severity that provide for the recognition of complex conditions based on multiple clinical cues identified from medical findings from a clinical text. In this regard, example embodiments parse the clinical text using natural language processing techniques, which aids in the identification of the clinical cues by identifying the medical findings and providing a clinical context that, in conjunction with the medical findings, inform clinical cue recognition.

Accordingly, example methods, apparatuses, and computer program products described herein are designed to receive a medical report, identify medical findings from the report, determine a context for each of the findings, identify clinical cues from the contextualized medical findings, generate condition signals from the clinical cues, and generate a condition alert indicating a significant incidental finding from the medical report.

In a first example embodiment, a computer-implemented method for identifying a condition of concern based on one or more significant incidental findings is provided. The method includes receiving, by communications circuitry of a computing device, a medical report, deriving, by natural language processing (NLP) circuitry of the computing device, a textual component of the medical report, and identifying, by the NLP circuitry of the computing device, one or more medical findings from the textual component. The method also includes determining, by the NLP circuitry of the computing device, a clinical context for each of the one or more medical findings, and identifying, by incidental finding circuitry of the computing device, one or more clinical cues comprising a gradient severity from the one or more medical findings. The method also further includes generating, by the incidental finding circuitry of the computing device, one or more condition signals comprising a gradient risk from the one or more clinical cues and generating, by the incidental finding circuitry of the computing device, a condition alert from the one or more condition signals, the condition alert indicating the condition of concern justified by the one or more condition signals.

In some embodiments, deriving the textual component of the medical report includes applying one or more natural language processing techniques to the medical report.

In some embodiments, the one or more natural language processing techniques include at least one of text normalization, tokenization, paraphrase and word variant recognition, acronym and abbreviation disambiguation, and document segmentation.

In some embodiments, the clinical context includes a set of attributes, modifiers, and clinical information that characterize a medical finding element, and determining the clinical context for each of the one or more medical findings includes determining, by the NLP circuitry of the computing device, one or more relationships between the one or more medical findings.

In some embodiments, determining the clinical context of the clinical element further includes one or more of determining, by the NLP circuitry, from the one or more relationships, one or more relation facts, wherein the one or more relation facts indicate that the medical finding is due to benign or less significant conditions, determining, by the NLP circuitry of the computing device, anatomical locations associated with the one or more medical findings, determining, by the NLP circuitry of the computing device, a patient history for one or more of the one or more medical findings, determining, by the NLP circuitry of the computing device, a clinical impression for one or more of the one or more medical findings, determining, by the NLP circuitry of the computing device, a clinical change for one or more of the one or more medical findings, determining, by the NLP circuitry of the computing device, a clinical qualification for one or more of the one or more medical findings, determining, by the NLP circuitry of the computing device, a clinical quantification for one or more of the one or more medical findings, or determining, by the NLP circuitry of the computing device, a clinical modifier for one or more of the one or more medical findings, where the clinical modifier includes at least characteristics which indicate the medical finding is not a significant incidental finding.

In some embodiments, identifying the one or more clinical cues from the one or more medical findings includes excluding from further processing, by the incidental finding circuitry of the computing device and based on the clinical context of the one or more medical findings, any of the one or more medical findings that are negated and not ancillary to the main purpose of the medical report, retrieving, by the incidental finding circuitry of the computing device and from a medical condition database, information regarding one or more conditions of concern associated with the one or more medical findings, wherein each of the conditions of concern is associated with a set of properties and rules for identifying clinical cues and clinical signals associated with the medical condition, identifying, by the incidental finding circuitry of the computing device and using the condition of concern, one or more clinical cues from the one or more medical findings, and determining, by the incidental finding circuitry of the computing device, a gradient severity score for each of the one or more the clinical cues.

In some embodiments, generating the one or more condition signals includes identifying, by the incidental finding circuitry of the computing device and from the one or more clinical cues, one or more condition signals for the condition of concern and determining, by the incidental finding circuitry of the computing device, a gradient risk level for each of the one or more condition signals, wherein the gradient risk level is determined from the one or more clinical cues in combination with predefined risk levels.

In some embodiments, generating the condition alert includes determining, by the incidental finding circuitry of the computing device, that one or more condition signals have been generated from the medical report, and generating, by the incidental finding circuitry of the computing device, the condition alert, wherein the condition alert specifies the condition of concern and the determined risk level.

In some embodiments, the computer implemented method for identifying a condition of concern based on one or more significant incidental findings further includes outputting, by communications circuitry of the computing device, the condition alert indicating the significant incidental finding.

In another example embodiment, an apparatus for identifying a condition of concern based on one or more significant incidental findings is provided. The apparatus includes communications circuitry configured to receive a medical report. The apparatus also includes natural language processing (NLP) circuitry configured to derive a textual component of the medical report, identify one or more medical findings from the textual component, and determine a clinical context for each of the one or more medical findings. The apparatus may also include incidental finding circuitry configured to identify one or more clinical cues comprising a gradient severity from the one or more medical findings, generate one or more condition signals comprising a gradient risk, from the one or more clinical cues, and generate a condition alert from the one or more condition signals, the condition alert indicating the condition of concern justified by the one or more condition signals.

In some embodiments of the apparatus, the NLP circuitry is configured to derive the textual component of the medical report by applying one or more natural language processing techniques to the medical report.

In some embodiments of the apparatus, the one or more natural language processing techniques include at least one of text normalization, tokenization, paraphrase and word variant recognition, acronym and abbreviation disambiguation, and document segmentation.

In some embodiments of the apparatus, the clinical context includes a set of attributes, modifiers, and clinical information that characterize a medical finding element and wherein to determine the clinical context for each of the one or more medical findings the NLP circuitry is further configured to determine one or more relationships between the one or more medical findings.

In some embodiments of the apparatus the NLP circuitry is further configured to determine, from the one or more relationships, one or more relation facts, wherein the one or more relation facts indicate that the medical finding is due to benign or less significant conditions, determine anatomical locations associated with the one or more medical findings, determine a patient history for one or more of the one or more medical findings, determine a clinical impression for one or more of the one or more medical findings, determine a clinical change for one or more of the one or more medical findings, determine a clinical qualification for one or more of the one or more medical findings, determine a clinical quantification for one or more of the one or more medical findings, or determine a clinical modifier for one or more of the one or more medical findings, where the clinical modifier includes at least characteristics which indicate the medical finding is not an incidental finding.

In some embodiments of the apparatus, in order to identify the one or more clinical cues from the one or more medical findings the incidental finding circuitry is further configured to exclude, based on the clinical context of the one or more medical findings, from further processing one or more medical findings that are negated and not ancillary to the main purpose of the medical report, retrieve from a medical condition database information regarding one or more conditions of concern associated with the one or more medical findings, wherein each of the conditions of concern is associated with a set of properties and rules for identifying clinical cues and clinical signals associated with the medical condition, identify, using the condition of concern, one or more clinical cues from the one or more medical findings, and determine a gradient severity score for each of the one or more the clinical cues.

In some embodiments of the apparatus, in order to generate the one or more condition signals the incidental finding circuitry is further configured to identify, from the one or more clinical cues, one or more condition signals for the condition of concern, and determine a gradient risk level for each of the one or more condition signals, wherein the gradient risk level is determined from the one or more clinical cues in combination with predefined risk levels.

In some embodiments of the apparatus, in order to generate the condition alert the incidental finding circuitry is further configured to determine that one or more condition signals have been generated from the medical report, and generate the condition alert, wherein the condition alert specifies the condition of concern and the determined risk level.

In some embodiments of the apparatus, the communication circuitry is further configured to output the condition alert indicating the significant incidental finding.

In yet another example embodiment, a non-transitory computer-readable storage medium for identifying a condition of concern based on one or more significant incidental findings is provided. The non-transitory computer-readable storage medium storing program code instructions that, when executed, cause a computing device to receive a medical report, derive a textual component of the medical report, identify one or more medical findings from the textual component, and determine a clinical context for each of the one or more medical findings. The program code instructions, when executed, further cause the computing device to identify one or more clinical cues comprising a gradient severity from the one or more medical findings, generate one or more condition signals comprising a gradient risk, from the one or more clinical cues, and generate a condition alert from the one or more condition signals, indicating the condition of concern justified by the one or more condition signals.

In some embodiments, the program code instructions, when executed, further cause the computing device to identify, from the one or more clinical cues, one or more condition signals for the condition of concern, determine a gradient risk level for each of the one or more condition signals, wherein the gradient risk level is determined from the one or more clinical cues in combination with predefined risk levels, determine that one or more condition signals have been generated from the medical report, and generate the condition alert, wherein the condition alert specifies the condition of concern and the determined risk level.

The above summary is provided merely for purposes of summarizing some example embodiments to provide a basic understanding of some aspects of the invention. Accordingly, it will be appreciated that the above described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Figure 1:
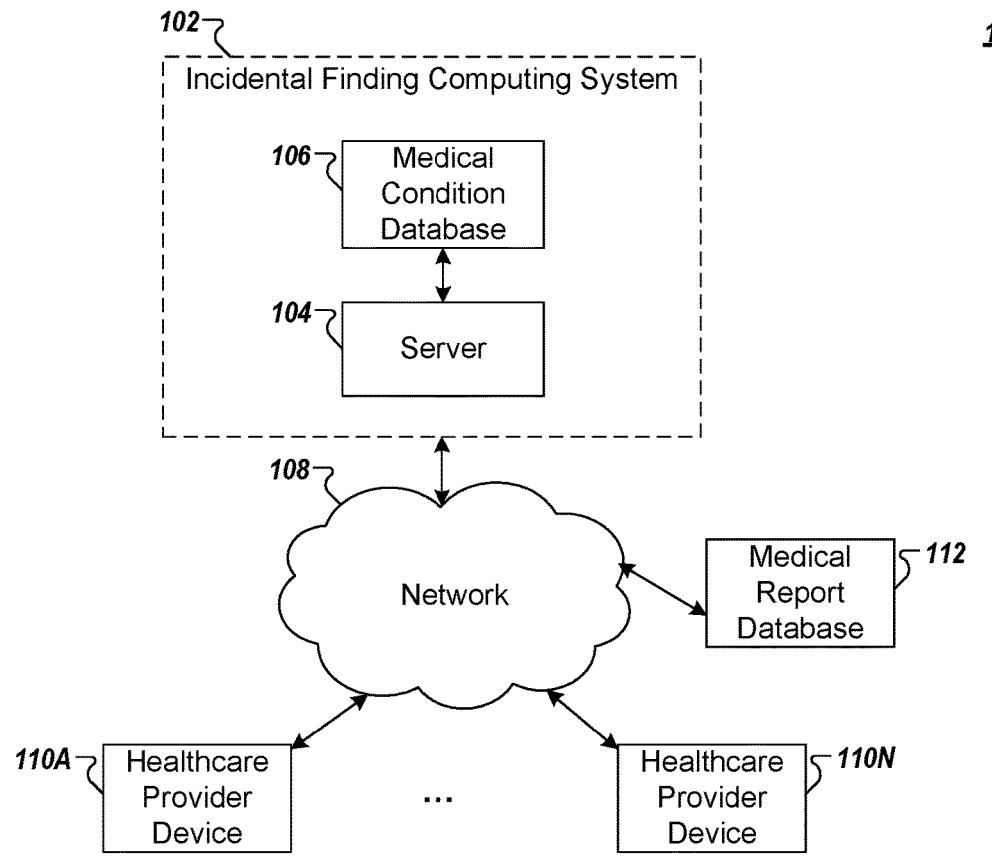
Figure 2:
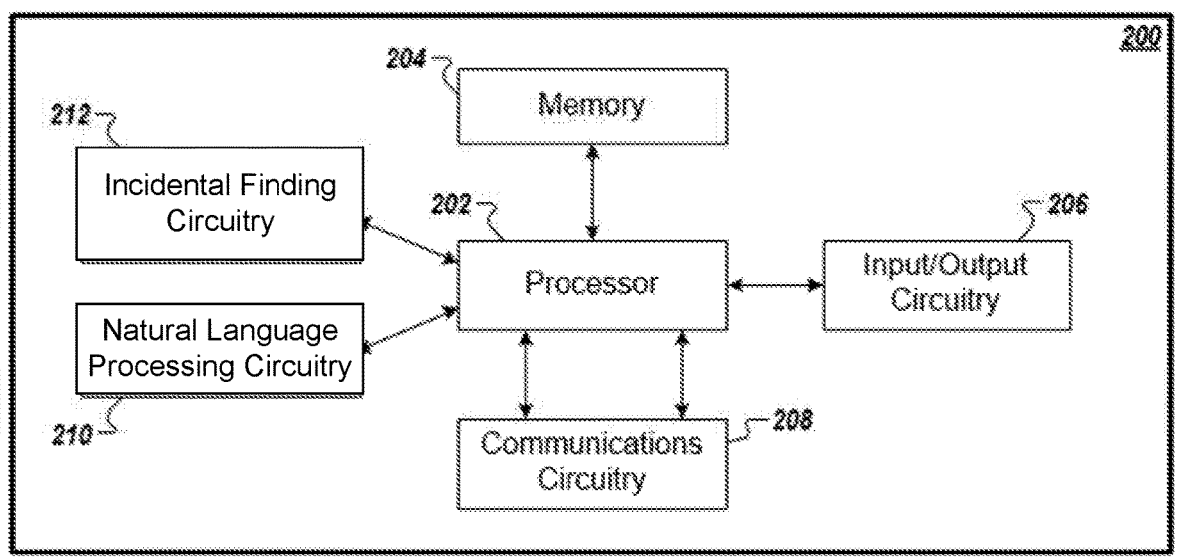
Figure 3:
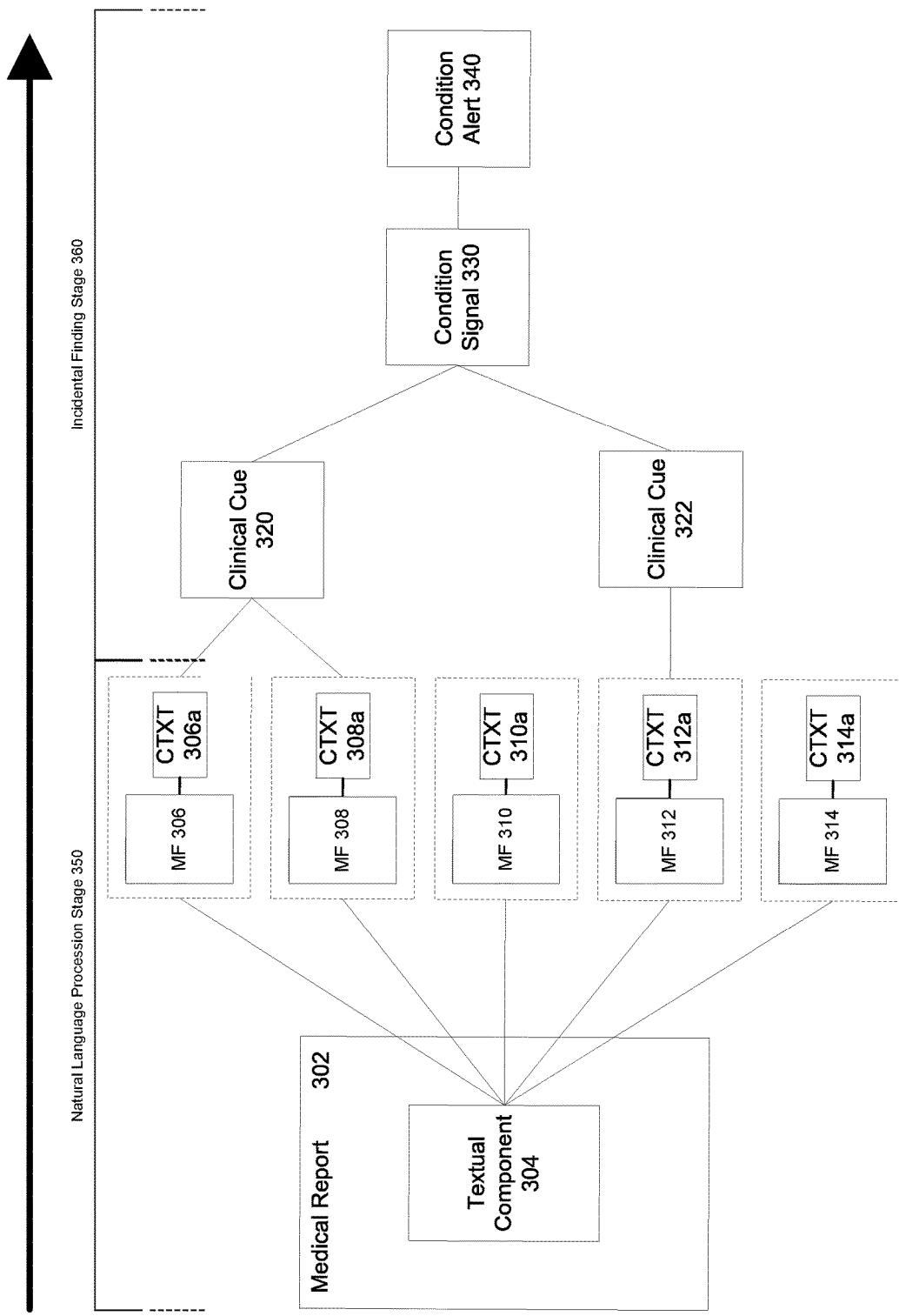
Figure 4:
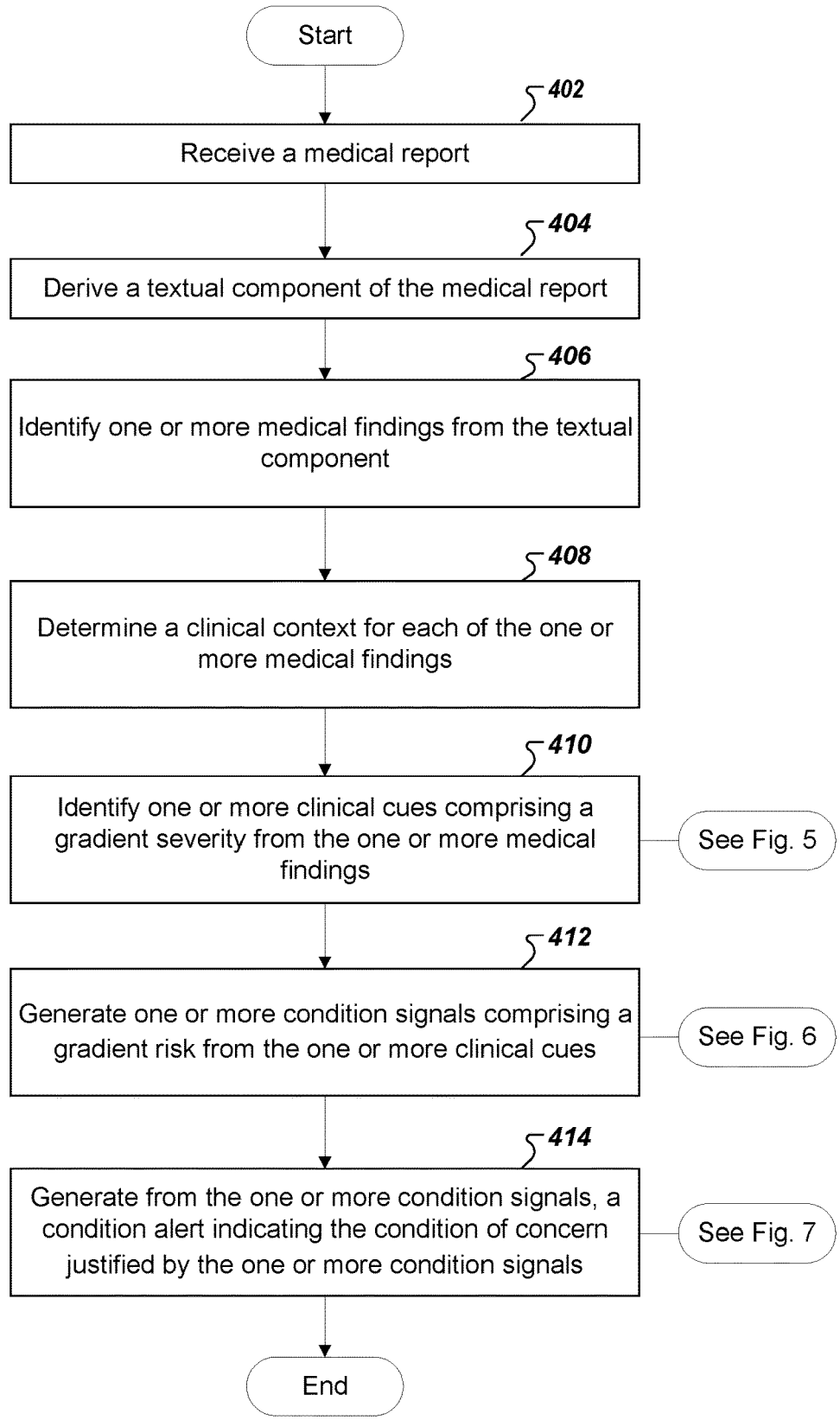
Figure 5:
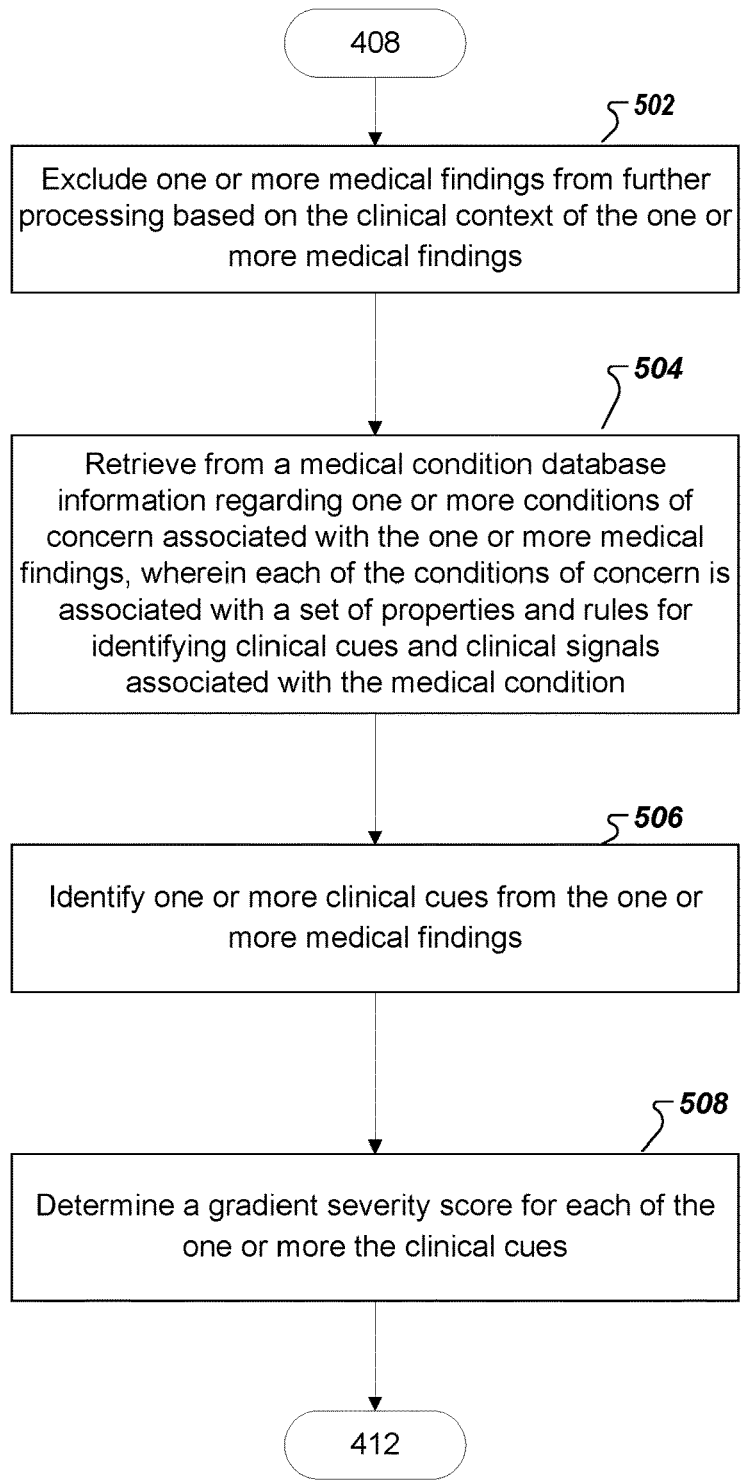
Figure 6:
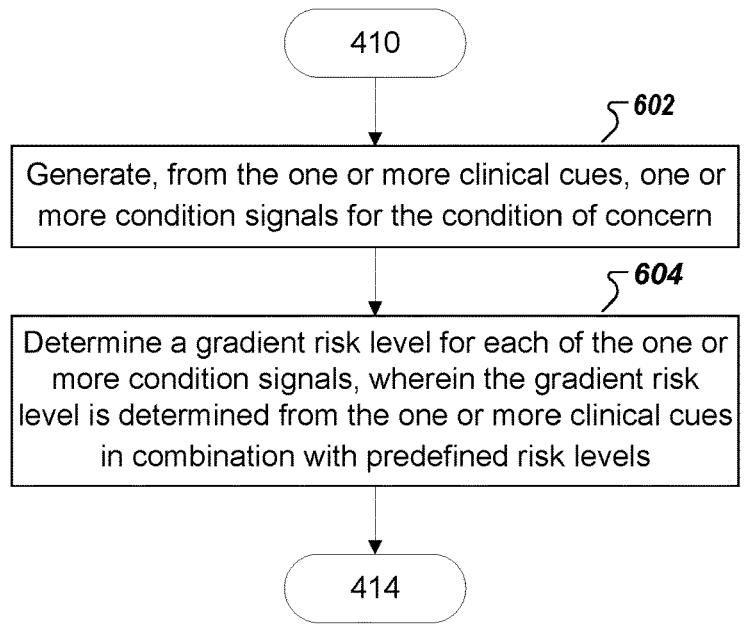
Figure 7:
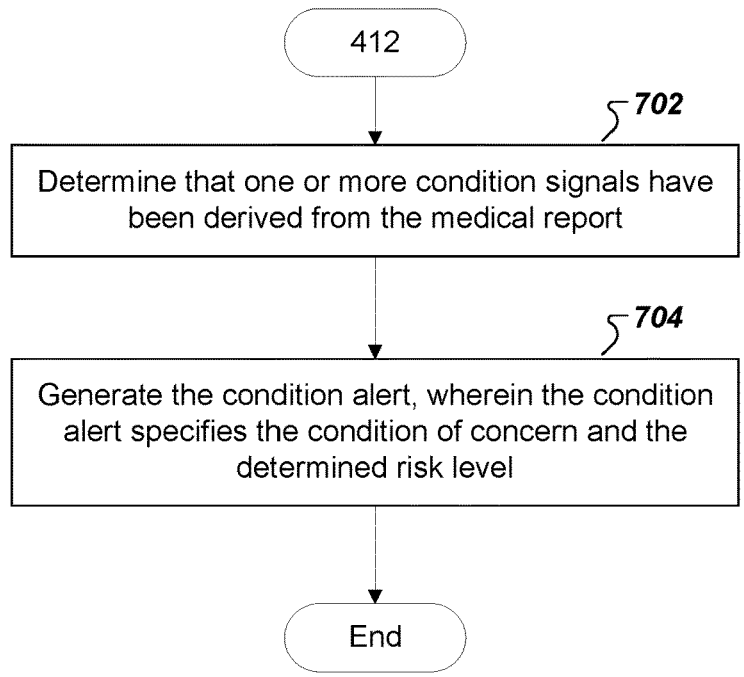

Having thus described certain example embodiments of the present disclosure in general terms, reference will now be made to the accompanying drawings, which are not necessarily drawn to scale, and wherein:

FIG. 1 shows an example system diagram, in accordance with an example embodiment of the present invention;

FIG. 2 illustrates a schematic block diagram of circuitry used in association with a significant incidental finding computing device, in accordance with some example embodiments;

FIG. 3 illustrates an example block process from a medical report to a condition alert, in accordance with some example embodiments;

FIG. 4 illustrates a flowchart describing example operations for identifying a significant incidental finding, in accordance with some example embodiments;

FIG. 5 illustrates a flowchart describing additional example operations for identifying a significant incidental finding, in accordance with some example embodiments;

FIG. 6 illustrates a flowchart describing additional example operations for identifying a significant incidental finding, in accordance with some example embodiments; and FIG. 7 illustrates a flowchart describing additional example operations for identifying a significant incidental finding, in accordance with some example embodiments.

DETAILED DESCRIPTION

Various embodiments of the present invention will now be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

As used herein, the terms "data," "content," "information," and similar terms may be used interchangeably to refer to data capable of being transmitted, received, and/or stored in accordance with embodiments of the present invention. Thus, use of any such terms should not be taken to limit the spirit and scope of embodiments of the present invention. Further, where a first computing device is described herein to receive data from a second computing device, it will be appreciated that the data may be received directly from the second computing device or may be received indirectly via one or more intermediary computing devices, such as, for example, one or more servers, relays, routers, network access points, base stations, hosts, and/or the like, sometimes referred to herein as a "network." Similarly, where a first computing device is described herein to send data to a second computing device, it will be appreciated that the data may be sent directly to the second computing device or may be sent indirectly via one or more intermediary computing devices, such as, for example, one or more servers, relays, routers, network access points, base stations, hosts, and/or the like.

As used herein, the term "medical finding" refers to any health related findings from a medical report.

As used herein, the term "clinical cue" refers to an individual clinical concept that may contribute (when in a collection with other cues, contexts and qualifiers) to the identification of an incidental finding pertinent to a condition of concern.

As used herein, the term "condition signal" refers to a combination of one or more clinical cues along with criteria about their contexts and attributes that together would generate a positive identification of an incidental finding.

As used herein, the term "condition alert" refers to an alert generated in response to the generation of a clinical signal and indicates that a significant incidental finding is present.

As used herein, the term "significant incidental findings" refers to one or more medical findings that are significant and should induce follow-up by a medical professional.

System Architecture and Example Apparatus

Systems for identification of significant incidental findings from medical reports may be embodied by any of a variety of devices. For example, an apparatus employed in an example embodiment may be embodied by a networked device, such as a server or other network entity, configured to communicate with one or more devices, such as one or more client devices. Additionally or alternatively, the computing device may include fixed computing devices, such as a personal computer or a computer workstation. Still further, example embodiments may be embodied by any of a variety of mobile terminals, such as a portable digital assistant (PDA), mobile telephone, smartphone, laptop computer, tablet computer, or any combination of the aforementioned devices.

In this regard, FIG. 1 discloses an example computing system within which embodiments described herein may operate. Healthcare providers including doctors, pharmacists, hospitals, professional, inpatient, outpatient, ancillary, or pharmaceutical providers may submit medical reports, for example a radiology report, to an Incidental Finding (IF) computing system 102 via a network 108 (e.g., the Internet, or the like) using computing devices 110A through 110N, respectively.

The computing devices 110A through 110N, may be embodied by any computing devices known in the art. For example, these devices may include desktop computers, laptop computers, smartphones, netbooks, tablet computers, wearable devices, and/or any combination of devices or entities adapted to perform the functions, operations, and/or processes described herein, and the electronic data may be provided using various transmission modes and/or protocols associated with these devices.

Additionally or alternatively, the healthcare providers, and other third parties may interact with the IF computing system 102 via a web browser. As yet another example, the devices 110A-110N may include various hardware or firmware designed to interface with the IF computing system 102 (e.g., where an example device 110 is a purpose-built device offered for communicating with the IF computing system 102, such as a kiosk).

Additionally or alternatively, IF computing system 102 may interact with a medical report database 112 configured to store medical reports from one or more healthcare providers. In some examples medical report database may comprise a database maintained by a third party provider, wherein the database may comprises medical records systems, document management systems, or chart repositories, and wherein the medical reports are provided to server 104 through network 108. In some examples, medical report database 112 may comprise a local component of IF computing system 102 or database 106. The medical reports may comprise any report or set of reports describing a medical exam or patient treatment. This may include pathology reports, lab reports, emergency medicine reports, operative reports, nursing notes, or any other medical document including natural language.

The IF computing system 102 may comprise a server 104 in communication with a medical condition database 106. The server 104 may be embodied as a computer or computers as known in the art. The server 104 may receive the electronic data from various sources, including but not necessarily limited to the devices 110A-110N and database 112, and may be operable to receive and process medical reports and records provided by these devices.

The medical condition database 106 may be embodied as a data storage device such as a Network Attached Storage (NAS) device or devices, or as a separate database server or servers. The medical condition database 106 includes information accessed and stored by the server 104 to facilitate the operations of the IF computing system 102. For example, the medical condition database 106 may include, without limitation: user account credentials for system administrators, healthcare providers, and other third parties; and sets of structured data (e.g., relational databases) correlating medical conditions with medical findings and attributes/context of the medical findings that are known or determined via processing of the records by the IF computing system 102, and/or the like. As may be most relevant to embodiments described herein, medical condition database 106 may include medical condition descriptions associated with the one or more medical findings, wherein each of the medical condition descriptions comprises properties and rules for identifying clinical cues and condition signals associated with corresponding medical findings.

Example Apparatus For Implementing Embodiments of the Present Invention

The server 104 may be embodied by one or more computing devices, such as apparatus 200 shown in FIG. 2. As illustrated in FIG. 2, the apparatus 200 may include a processor 202, a memory 204, input/output circuitry 206, communications circuitry 208, natural language processing (NLP) circuitry 210, and incidental finding circuitry 212. The apparatus 200 may be configured to execute the operations described above in connection with FIG. 1 and below in connection with FIGS. 4-7. Although these components 202-212 are described in part using functional terminology, it should be understood that implementation of the corresponding functions necessarily requires the use of particular hardware. It should also be understood that certain of these components 202-212 may include similar or common hardware. For example, two sets of circuitry may both leverage use of the same processor, network interface, storage medium, or the like to perform their associated functions, such that duplicate hardware is not required for each set of circuitry. The use of the term "circuitry" as used herein with respect to components of the apparatus therefore includes particular hardware configured to perform the functions associated with the particular circuitry described herein.

Of course, while the term "circuitry" should be understood broadly to include hardware, in some embodiments it may also include software that configures operation of the hardware. In some embodiments, "circuitry" may include processing circuitry, storage media, network interfaces, input/output devices, and the like. In some embodiments, other elements of the apparatus 200 may provide or supplement the functionality of particular circuitry. For example, the processor 202 may provide processing functionality, the memory 204 may provide storage functionality, the communications circuitry 208 may provide network interface functionality, and the like.

The processor 202 (and/or co-processor or any other processing circuitry assisting or otherwise associated with the processor) may be in communication with the memory 204 via a bus for passing information among components of the apparatus. The memory 204 may be non-transitory and may include, for example, one or more volatile and/or non-volatile memories. In other words, the memory may be an electronic storage device (e.g., a computer readable storage medium). The memory 204 may be configured to store information, data, content, applications, instructions, or the like, for enabling the apparatus to carry out various functions in accordance with example embodiments of the present invention.

The processor 202 may be embodied in a number of different ways and may, for example, include one or more processing devices configured to perform independently. Additionally or alternatively, the processor may include one or more processors configured in tandem via a bus to enable independent execution of instructions, pipelining, and/or multithreading. The use of the term "processing circuitry" may be understood to include a single core processor, a multi-core processor, multiple processors internal to the apparatus, and/or remote or "cloud" processors.

In an example embodiment, the processor 202 may be configured to execute instructions stored in the memory 204 or otherwise accessible to the processor. Alternatively or additionally, the processor may be configured to execute hard-coded functionality. As such, whether configured by hardware or software methods, or by a combination of hardware with software, the processor may represent an entity (e.g., physically embodied in circuitry) capable of performing operations according to an embodiment of the present invention while configured accordingly. Alternatively, as another example, when the processor is embodied as an executor of software instructions, the instructions may specifically configure the processor to perform the algorithms and/or operations described herein when the instructions are executed.

In some embodiments, the apparatus 200 may include input/output circuitry 206 that may, in turn, be in communication with processor 202 to provide output to a user and, in some embodiments, to receive an indication of user input. The input/output circuitry 206 may comprise a user interface and may include a display and may comprise a web user interface, a mobile application, a client device, a kiosk, or the like. In some embodiments, the input/output circuitry 206 may also include a keyboard, a mouse, a joystick, a touch screen, touch areas, soft keys, a microphone, a speaker, or other input/output mechanisms. The processor and/or user interface circuitry comprising the processor may be configured to control one or more functions of one or more user interface elements through computer program instructions (e.g., software and/or firmware) stored on a memory accessible to the processor (e.g., memory 204, and/or the like).

The communications circuitry 208 may be any means such as a device or circuitry embodied in either hardware or a combination of hardware and software that is configured to receive and/or transmit data from/to a network and/or any other device, circuitry, or module in communication with the apparatus 200. In this regard, the communications circuitry 208 may include, for example, a network interface for enabling communications with a wired or wireless communication network. For example, the communications circuitry 208 may include one or more network interface cards, antennae, buses, switches, routers, modems, and supporting hardware and/or software, or any other device suitable for enabling communications via a network. Additionally or alternatively, the communication interface may include the circuitry for interacting with the antenna(s) to cause transmission of signals via the antenna(s) or to handle receipt of signals received via the antenna(s).

The NLP circuitry 210 and incidental finding circuitry 212 may be any means such as a device or circuitry embodied in either hardware or a combination of hardware and software that is configured to perform the corresponding functions of these components that are described herein.

As will be appreciated, any such computer program instructions and/or other type of code may be loaded onto a computer, processor or other programmable apparatus's circuitry to produce a machine, such that the computer, processor other programmable circuitry that execute the code on the machine create the means for implementing various functions, including those described herein.

In some embodiments, one or more external systems (such as a remote cloud computing and/or data storage system) may also be leveraged to provide at least some of the functionality discussed herein.

As described above and as will be appreciated based on this disclosure, embodiments of the present invention may be configured as methods, mobile devices, backend network devices, and the like. Accordingly, embodiments may comprise various means including entirely of hardware or combinations of software and hardware. Furthermore, embodiments may take the form of a computer program product stored on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

Example Operations Performed By the IF Computing Device

Having described the circuitry comprising embodiments of the present invention, it should be understood that the IF computing system 102 may advantageously identify significant incidental findings in a number of ways. In accordance with example embodiments, FIG. 3 illustrates an examples block process showing the processing of a medical report to the generation of a condition alert, while FIGS. 4-7 illustrate flowcharts containing specific operations performed to accurately and selectively identify significant incidental findings from a medical report, wherein the specific operations process, determine, identify, or generate the different components shown in FIG. 3.

Turning now to FIG. 3, an example block diagram is provided that illustrates a process that begins by reviewing a medical report and eventually produces a condition alert, in accordance with some example embodiments. It should be understood that while FIG. 3 illustrates certain steps of the methods described in FIGS. 4-7, it should be understood that FIG. 3 illustrates only one example of a framework for identifying significant incidental findings contemplated herein.

The process shown in FIG. 3 may be performed by IF computing system 102, with the assistance of, and/or under the control of a computing device such as apparatus 200. The process begins with the IF computing system 102 initiating a natural language processing (NLP) stage 350 (described in greater detail in relation to operations 404 through 408 of FIG. 4) to analyze a received medical report 302. This NLP stage 350 identifies a textual component 304 of the medical report 302, which may include the textual component 304 in addition to non-textual components such as graphs, charts, unrelated numerical data, and images. In some examples the medical report may comprise one or more documents and one or more textual components. The NLP stage 350 further performs at least text normalization, tokenization, acronym disambiguation, document segmentation, concept boundary identification and context recognition on the textual component 304 (as described in greater detail in connection with operation 404). The NLP stage 350 identifies medical findings such as MF 306-314 from the textual component 304 (as described in greater detail in connection with operation 406). In addition, the NLP stage, further determines a corresponding context for each of the medical findings, shown in FIG. 3 as CTXT 306a-314a (as described in greater detail in connection with operation 408 below). For example, an output of the NLP stage may include a medical finding, a relationship between one or more of the medical findings to a cause of the medical finding (e.g., "X due to Y"), and anatomical regions described in the medical report that correspond to the medical finding. In some cases, these relationships may be a relation fact indicating that the medical finding is due to benign or less significant conditions.

For example, the textual component 304 may include the derived natural language text "lung consolidation seen in the lungs, likely due to patient's current case of pneumonia." The output from the NLP processing of this step may include the medical finding MF 306 (consolidation) and the medical finding MF 308 (pneumonia). The context CTXT 306a may include "location: lungs, relation fact: MF 306 due to MF 308".

The context corresponding to the medical findings may include a collection of modifiers, or attributes, that capture the context of the medical finding. For example, a textual component 304 may include "no pulmonary nodules," the NLP stage will output a medical finding, such as MF 314 that represents the medical finding of "pulmonary nodules", and a related context, such as MF 314a, which includes a contextual modifier indicating that pulmonary modules are ruled out or excluded. Recognizing medical findings and their associated context in the NLP processing represents an advance over historical methods for identifying medical findings, such as keyword search methods, because it provides precision in identifying each medical finding (even those that are ruled out or excluded) and the context (i.e. ruled out (excluded), or not a concern) can be used in deciding whether to take further action regarding the medical finding.

While the medical findings 306-314 and the contexts 306a-314a are primarily directed toward identifying and describing the medical findings in the textual component 304, they may also include data presenting the beginning and ending character offsets of the location of the corresponding medical findings in the medical report 302, thus enabling a user to trace all references to a specific component of the medical report 302 and a specific location in the textual component 304. The combined medical findings and contexts are then outputted from the NLP stage and passed into an incidental finding resolver or an incidental finding (IF) stage 360.

The IF computing system 102 initiates the IF stage 360 to consider the medical findings in context, and applies logical rules to identify individual clinical cues, such as clinical cue 320 and clinical cue 322, from the medical findings that are salient to a condition of concern (as described below in connection with operation 410 and FIG. 5). The IF stage is further described in relation to operations 410 through 414 of FIG. 4 and FIGS. 5-7. In general, the IF stage includes determining gradient levels that apply to particular clinical cues, to categorize those cues by severity as "strong" or "weak" based on how strongly the cue correlates with the condition of concern. Combinations of clinical cues, such as the clinical cue 320 and the clinical cue 332 that justify a follow-up investigation regarding a serious disease or condition of concern are then used to prompt the generation of a condition signal, such as condition signal 330 (as described in connection with operation 412 and FIG. 6). Like the clinical cues, the condition signals also may be categorized with gradient levels that can have varying risks (e.g., HIGH, MEDIUM, and LOW). In some examples, the risk level is pre-determined by physician subject matter experts for each particular medical condition, in combination with the particular clinical cues identified in the condition signal. In some examples, results and evaluations (e.g., data) from previously processed reports are applied as feedback in a machine learning process utilizing the Medical Condition Database (106) to refine and enhance the system-determined risk levels. In some examples, the generation of a condition alert may be determined by the risk levels of the generated condition signals and by the severities of the precursor clinical cues. For example, there may be multiple clinical cues that generate multiple condition signals, and multiple condition signals that generate a condition alert. Based on the severity of individual cues and the risk levels of individual condition signals, IF computing system may filter which conditions alerts are generated. In some examples, a condition alert may always be generated if a condition signal is generated, but the generated alerts may be filtered such that it is not visible to a user. As described above, the utilization of gradient severities and risk levels allows for selective targeting and avoids over-alerting based on the incidental findings from a report.

In other embodiments, however, generation of condition alerts is not filtered based on the severity of clinical cues or the risk level of condition signals, but are filtered based on predetermined criteria selected by a client. For instance, a client can choose to receive all condition alerts regardless of severity or risk of the underlying clinical cues and condition signals that is possible. Alternatively, a client can choose to receive only those condition alerts stemming from high risk condition signals or high severity clinical cues.

In any event, the clinical cue severities and condition signal risks thus comprise a "gradient" score that drives the overall risk of the alert, and can be used as a filter determining which condition alerts are generated (either by default or as specified by a client). In some embodiments, clinical cue severity comprises one of "strong" or "weak" and risk comprises one of "low", "medium", or "high". In other examples, however, the clinical cue severity and risk may comprise numerical (real number) scores or other gradient type scoring.

The generation of the one or more condition signals then drives the generation of a condition alert 340 (as described in connection with operation 414 and FIG. 7). The condition alert 340 may indicate the condition of concern identified from the clinical cues, the condition signals, and the corresponding risk levels. The condition alert 340 can be used, for instance, to alert a medical professional of a significant incidental finding, who in turn can quickly access a level of concern (risk) for the incidental finding and identify the specific medical findings from the report which caused the generation of the alert.

For example, the IF stage generates a condition alert 340 for follow-up for cancer when it detects one or more condition signals, such as condition signal 330, that are concerning for potential cancer. In some examples, the condition signals 330 may include gradient levels describing the signal such as "Strong cue," "Weak cue with change," or "Weak cue with qualification." The condition alert 340 may further include with each condition signal 330 the one or more clinical cues (e.g., clinical cue 320 and/or clinical cue 322) that prompted the condition alert 340 that correspond directly with the medical findings processed from the text in the NLP stage.

The generation of the condition alert 340 is ultimately governed by rules for each condition of concern, and the rules may be stored in and retrieved from a medical condition database 106. An example of a medical condition rule for generating a clinical signal 330 for cancer may be the following:

If there is:
  a weak cue (e.g. nodule) that has changed or is changing (e.g. previously unseen), and
  no explicit suggestion that the cue is due to a benign condition (no mention of "nodule possibly due to infection"), and
  no history of cancer
Generate a condition signal with a MEDIUM risk including: "Weak cue with change."

An example for generating a condition alert 340 utilizing the framework of FIG. 3 may include:
Example: Generate Condition alert 340 from a condition signal 330 for cancer if there is:
  A weak cue 322 from MF 312 (lung consolidation)
  That has changed or is changing from CTXT 312*a* (worsening)
  With no explicit suggestions that it is due to a benign condition (e.g. no relationship to another medical finding such as an infection)
  And no history of cancer identified from CTXT 312*a*.
  And a condition signal indicates a MEDIUM risk.

Turning now to FIG. 4, the provided flowchart illustrates a detailed sequence of example operations identifying significant incidental findings, in accordance with some example embodiments. As noted previously, these operations may be performed by IF computing system 102, with the assistance of, and/or under the control of a computing device such as server 104, which may be embodied by apparatus 200.

In operation 402, apparatus 200 includes means, such as input/output circuitry 206, communications circuitry 208, or the like, for receiving a medical report. The medical reports may be received from a variety of sources, such as from providers using one or more healthcare provider devices 110A-110N, one or more medical report databases 112, one or more insurers, or the like. Alternatively, the medical report can be input by a user, such as by directly communicating with input/output circuitry 206 of the apparatus 200. The medical report may comprise computer-generated text, text generated by a medical professional authoring the report, graphs, images, tables/charts, computer readouts, identification information, such as patient information (e.g. demographic information, gender, and age), and/or other data typically included in medical reports. The medical reports, when received, may be in raw data form and the apparatus 200 may thus include means, such as processor 202, NLP circuitry 210, or the like, for organizing the report into discrete components, such as textual component 304 shown in FIG. 3. In some examples, the medical reports comprise professional, inpatient, outpatient, ancillary, or other medical records, such as a radiology report, a doctor's visit summary, or other data including patient level data indicating medical information about the patient and data describing the purpose or reason for the generation of the report.

In operation 404, apparatus 200 includes means, such as NLP circuitry 210 or the like, for deriving a textual component of the medical report. In some examples, deriving the textual component of the medical report may include processing the textual parts of the medical report to computer readable text from a natural language text. In some examples, deriving the textual component of the medical report uses one or more natural language processing techniques, including at least text normalization, tokenization, acronym disambiguation, paraphrase and word variant recognition, acronym and abbreviation disambiguation, and document segmentation to the medical report. Examples of such NLP techniques are described in greater detail in U.S. Pat. Nos. 6,915,254, 7,908,552, U.S. patent application Ser. No. 11/735,254, and U.S. patent application Ser. No. 12/185, 754, the entire contents of which are incorporated herein by reference.

The use of NLP techniques to derive the textual component of the medical report ensures that medical findings and subsequent clinical cues are identified regardless of the format (e.g., paraphrase, synonymy, abbreviations, acronyms, hypernyms, hyponyms, etc. . . . ) in which they are received. Such techniques thus facilitate more comprehensive recognition of clinical indicators and medical findings within medical reports. For example, a medical provider writing a given medical report may use abbreviations which are standard in describing the images and data gathered for the report, along with their own impressions and interpretations of the data.

In operation 406, apparatus 200 includes means, such as NLP circuitry 210 or the like, for identifying one or more medical findings from the textual component. In some examples, medical findings are defined by clinical information stored in a NLP knowledge base. That knowledge base includes lexicographic/linguistic information about clinical terminology and language, as well as rules of logic used to combine and refine such information. For example, the IF system 102 utilizes the knowledge base to identify the various ways of referring to procedures such as the removal of a body part, the various ways of referring to a body part such as a kidney, the various ways of indicating laterality such as right/left, and rules that allow for the appropriate combination of body part and laterality to obtain a specific body part, as well as rules that indicate removal of that body part is a possible procedure. In some examples, lexicographic/linguistic information and rules are deployed/applied via the NLP circuitry 210. In some examples, NLP circuitry 210 is configured to ignore information that is not directly pertinent to a clinical indicator or its attributes and context. Examples of such NLP techniques are described in greater detail in U.S. Pat. No. 6,915,254.

In operation 408, apparatus 200 includes means, such as NLP circuitry 210 or the like, for determining a clinical context for each of the identified medical findings. Determining the clinical context may include determining a patient history for one or more of the one or more medical findings (i.e. history of a certain condition), determining a clinical impression from the medical report, such as a medical impression from an impressions section of the report, for at least one of the one or more medical findings (i.e. a medical provider provides their professional impression of the medical finding), determining a clinical change for one or more of the one or more medical findings (e.g. "worsening", "growing" etc.). Determining the clinical context may also include determining a clinical qualification (e.g. "worsening") for one or more of the one or more medical findings, determining a clinical quantification for one or more of the one or more medical findings (e.g. size or number), and determining a clinical modifier for one or more of the one or more medical findings, wherein the clinical modifier comprises at least characteristics which indicate the absence of a medical finding is not a significant incidental finding (e.g. "no pulmonary nodules"). The use of NLP techniques described herein may facilitate any or all of these clinical context determinations.

The use of NLP in operations 404-408 to extract not just medical findings, but the clinical context related to each identified medical finding ultimately provides a robust and comprehensive set of data from which it is possible to identify clinical cues that are pertinent to a condition of concern. Recognition of medical findings with an appropriate clinical context is thus essential for determining the significance of clinical cues and generating condition signals and helps to ensure more accurate condition alerts and indication of significant incidental findings (i.e., by reducing the possibility of false warnings that can unnecessarily worry a patient, lead to unnecessary additional exams and treatment, or otherwise detract from primary care.)

In operation 410, apparatus 200 includes means, such as incidental finding circuitry 212, or the like, for identifying one or more clinical cues comprising a gradient severity from the one or more medical findings. This operation is described in greater detail in relation to the operations described in FIG. 5.

In operation 412, apparatus 200 includes means, such as incidental finding circuitry 212, or the like, for deriving one or more condition signals comprising a gradient risk from the one or more clinical cues. This operation is described in greater detail in relation to the operations described in FIG. 6.

In operation 414, apparatus 200 includes means, such as input/output circuitry 206, communications circuitry 208, incidental finding circuitry 212, or the like, for generating a condition alert indicating the condition of concern justified by the one or more condition signals. The condition alert may be transmitted by apparatus 200 in any suitable manner to indicate identification of a significant incidental finding. This operation is described in greater detail in relation to the operations described in FIG. 7.

Turning now to FIG. 5, FIG. 5 illustrates a flowchart describing additional example operations for identifying a significant incidental finding, in accordance with some example embodiments. Specifically, FIG. 5 illustrates operations for identifying one or more clinical cues from the one or more medical findings in greater detail than that described in connection with operation 410 of FIG. 4. As noted previously, the operations for identifying clinical cues may be performed by IF computing system 102, with the assistance of, and/or under the control of a computing device such as server 104, which may be embodied by apparatus 200. As described below, apparatus 200 may be configured to identify clinical cues and a severity score for each of the clinical cues.

In operation 502, apparatus 200 includes means, such as incidental finding circuitry 210 or the like, for excluding one or more medical findings from further processing based on the clinical context of the one or more medical findings. Excluding the medical findings may include determining, from the clinical context, whether the medical finding relates to a condition of concern. For example, if the clinical context of a medical finding includes a modifier or is negated (i.e. "no pulmonary nodules"), then the apparatus 200 may exclude the medical finding. Other clinical context information which may rule out or exclude medical findings may include, for instance, the purpose of the report (i.e. "scan to identify tumor"), relationships to other medical findings (i.e. "lung consolidation due to infection"), patient history (i.e. previously identified mass, unchanged), or clinical impressions. The medical findings that are not excluded thus represent the set of medical findings that were not negated and that are ancillary to the main purpose of the exam (i.e., incidental findings), and which should be used to determine if a condition alert is needed because of the significance of an incidental finding. It should be understood that operation 502 may be optional in some instances, because it may in fact be the case that all of the identified medical findings are both not negated by the corresponding clinical context and also incidental to the purpose of the medical report, in which case none of the medical findings would actually be excluded. In other instances, at least the medical findings related to the primary purpose of the creating of the medical report will be excluded in operation 502.

In operation 504, apparatus 200 includes means, such as incidental finding circuitry 210 or the like, for retrieving, from a medical condition database, information regarding one or more conditions of concern associated with the one or more medical findings, wherein each of the conditions of concern is associated with a set of properties and rules for identifying clinical cues and clinical signals associated with the medical condition. In this regard, the one or more conditions of concern are associated with each medical finding that was not excluded in operation 502. In this regard, a condition of concern is associated with a set of properties and rules for identifying clinical cues and condition signals associated with the medical finding. For example, incidental finding circuitry 212 may retrieve a condition of concern for cancer if one or more of the non-excluded medical findings is a potential sign of cancer. For example, the medical finding or its corresponding clinical context may include one or more of a "tumor", "consolidation", "irregular density", or a clinical impression that indicates cancer. In this regard, the conditions of concern may be identified by the apparatus 200 and the corresponding information subsequently may be retrieved from the medical condition database. Alternatively, components of the medical findings and clinical contexts may be used as elements of a query of the medical condition database, which identifies the related conditions of concern and returns the associated conditions of concern to the apparatus 200. Either way, in this specific example, a condition of concern for cancer would be retrieved from the medical condition database based on the medical findings of a "tumor", "consolidation", "irregular density", or a clinical impression that indicates cancer. In some examples, the medical findings and corresponding clinical contexts may relate to several conditions of concerns, which may potentially require the subsequent identification of clinical cues and generation of condition signal and condition alert for each of the multiple conditions of concern. In this way, one medical finding may be identified as a clinical cue for multiple conditions of concern.

In operation 506, apparatus 200 includes means, such as incidental finding circuitry 212 or the like, for identifying one or more clinical cues from the one or more medical findings. This identification may be made based not only on the medical findings, but also on the corresponding clinical contexts and the set of conditions of concern and corresponding set of properties and rules for identifying clinical cues relevant to those conditions of concern. In one example, the properties and rules for identifying clinical cues and condition signals associated with the medical condition may include logical rules and properties for classifying or identifying medical findings (including the context of the medical findings) as clinical cues.

In operation 508 apparatus 200 includes means, such as incidental finding circuitry 210 or the like, for determining a severity score for each of the one or more the clinical cues identified in operation 506. In some examples, the severity of the clinical cues is in turn used to generate the one or more condition signals. The properties and rules used to identify the clinical cues may also be used to evaluate the medical findings and corresponding clinical contexts to apply a gradient severity level for the clinical cues, such as strong, weak, or moderate. For example, a weak clinical cue for cancer (condition of concern) may include "lung consolidation" or "lesion" or "nodule." In contrast, a strong clinical cue may include "malignancy" or "mass" or "tumor" or "neoplasm." In this way, the incidental finding circuitry uses the condition of concern properties and rules for identifying the clinical cues and, in some examples, assigning a clinical severity for each of the identified clinical cues. In some embodiments, the clinical severity is determined from consultation of a repository of clinical expert guidance in combination with data analysis and trending of results. Additionally or alternatively, machine learning methods may be applied to refine the clinical severity of individual certain clinical cues.

FIG. 6, in turn, illustrates a flowchart describing additional example operations for identifying the significance of an incidental finding, in accordance with some example embodiments. Specifically, FIG. 6 further illustrates additional operations related to generating one or more condition signals from the one or more clinical cues as described in operation 412 of FIG. 4. As noted previously, these operations may be performed by IF computing system 102, with the assistance of, and/or under the control of a computing device such as apparatus 200. As described below, apparatus 200 may be configured to identify clinical cues and a severity score for each of the clinical cues.

In operation 602, apparatus 200 includes means, such as incidental finding circuitry 210 or the like, for identifying, from the one or more clinical cues, one or more condition signals for the condition of concern. Generating the condition signals may, in some examples, be based on the severity of the clinical cues (i.e., strong ("cancer") or weak ("consolidation")). The properties and rules of the condition of concern may also include the logic for generating the condition signal. For example, a condition signal may be generated for a:
1. Strong clinical cue that is
   i. Not explicitly noted as unchanged since previous exam
   ii. Not explicitly attributed to benign conditions
   iii. Meets a quantificational requirement (e.g. minimum size)
2. Weak clinical cue that is
   i. Not explicitly attributed to benign conditions
   ii. Meets a quantificational requirement (e.g. minimum size)
   iii. AND explicitly noted as changed since previous exam
   iv. OR explicitly noted as abnormal or concerning
   v. OR explicitly called out for follow-up examination.

This architecture enables the IF computing system 102 to define and handle complex condition signals and selectively/accurately identify significant incidental findings. In some embodiments, clinical cues are interpreted with respect to condition signals, wherein where a condition signal is a collection of cues, their contexts, qualifiers, quantifiers and other factors (due to, follow-up, etc.), and pertinent associated logic that enables definition of complex conditions that cannot necessarily be identified accurately from a single cue, but more from a collection and enables selective targeting, reducing unnecessary warnings and giving system users filter control over which alerts are pursued.

In operation 604, apparatus 200 includes means, such as incidental finding circuitry 210 or the like, determining a risk level for each of the one or more condition signals. The risk level may be a stored value generated by the apparatus 200. In one example, to initially generate the stored risks levels for the various condition signals, every condition signal may initially have a medium risk level. This risk level may then be adjusted up to a high risk level or down to a low risk level according to predefined factors for determining risk. These predefined factors may include the clinical cues relevant to the condition signal, the context of the clinical cues and stored expert medical opinion(s), and apparatus 200 may evaluate these predefined factors to determine a more refined risk level for each condition signal. Alternatively, in some examples, the risk level may be assigned directly from the predefined factors or may be initialized at a low risk and adjusted from the low risk level if needed. Additionally or alternatively, determined risk levels can be reused as feedback in a machine learning module, such that the risk is further refined by past risk determinations. The gradient levels in both the clinical cue and condition signals operations ensure proper filtration of the system to avoid over- or under-generation of conditions alerts. Alerting based on a weak cue alone would often be unnecessary, but weak cues when augmented with additional context and attribute cues may identify a possible disease that would otherwise remain unnoticed. The risk level can also be utilized by a user in limiting or filtering what conditions should ultimately generate an alert. For example, a user could limit review to cancer alerts derived from condition signals with high risk levels.

Finally, FIG. 7 illustrates a flowchart describing additional example operations for identifying a significant incidental finding, in accordance with some example embodiments. Specifically, FIG. 7 further illustrates additional operations related to generating a condition alert from the one or more condition signals, indicating a significant incidental finding in operation 414 of FIG. 4. As noted previously, these operations may be performed by IF computing system 102, with the assistance of, and/or under the control of a computing device such as server 104, which may be embodied by apparatus 200. As described below, apparatus 200 may be configured to identify clinical cues and a severity score for each of the clinical cues.

In operation 702, apparatus 200 includes means, such as incidental finding circuitry 210 or the like, for determining whether one or more condition signals have been derived from the medical report. In response to determining that a signal was generated, the process advances to operation 704.

In operation 704, apparatus 200 includes means, such as incidental finding circuitry 210 or the like, generating the condition alert, wherein the condition alert specifies the condition of concern and the determined risk level. The condition alert may also be reported or outputted via a medical report, a flag that is inserted into an Electronic Medical Records chart, or an additional output indicator in a computer assisted coding application. In some examples, reporting the condition alert may be limited to specific conditions of concern selected by a user, such as a type of condition. In some examples, reporting may be also limited to disease signals that pass a predefined set of minimum risk/severity criteria, for example high risk.

The generation of the condition alert allows for a medical professional, despite their skill or knowledge, to be alerted to a significant incidental finding from a medical report. The medical provider can then follow-up quickly and efficiently, with confidence the indicated incidental finding is significant enough to require the time and attention necessary for the follow-up. The result is both better health outcomes for the patient and better use of medical provider resources.

FIGS. 4-7 illustrate flowcharts of the operation of an apparatus, method, and computer program product according to example embodiments of the invention. It will be understood that each block of the flowcharts, and combinations of blocks in the flowcharts, may be implemented by various means, such as hardware, firmware, processor, circuitry, and/or other devices associated with execution of software including one or more computer program instructions. For example, one or more of the procedures described above may be embodied by computer program instructions. In this regard, the computer program instructions which embody the procedures described above may be stored by a memory of an apparatus employing an embodiment of the present invention and executed by a processor of the apparatus. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture, the execution of which implements the functions specified in the flowchart blocks. The computer program instructions may also be loaded onto a computer or other programmable apparatus to cause a series of operations to be performed on the computer or other programmable apparatus to produce a computer-implemented process such that the instructions executed on the computer or other programmable apparatus provide operations for implementing the functions specified in the flowchart blocks.

Accordingly, blocks of the flowcharts support combinations of means for performing the specified functions and combinations of operations for performing the specified functions. It will be understood that one or more blocks of the flowcharts, and combinations of blocks in the flowcharts, can be implemented by special purpose hardware-based computer systems which perform the specified functions, or combinations of special purpose hardware and computer instructions.

In some embodiments, certain ones of the operations above may be modified or further amplified. Furthermore, in some embodiments, additional optional operations may be included. Modifications, amplifications, or additions to the operations above may be performed in any order and in any combination.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

The invention claimed is:

1. A computer-implemented method for identifying a condition of concern based at least in part on incidental medical findings, the method comprising:
  receiving, by circuitry, a dataset output by natural language processing circuitry, wherein the natural language processing circuitry is configured to:
    receive an electronic medical report, wherein the electronic medical report comprises a plurality of textual components and at least one non-textual component; and
    perform natural language processing, wherein the natural language processing comprises:
      (a) processing the plurality of textual components of the electronic medical report from natural language text to computer readable text by performing at least one of text normalization, tokenization, paraphrase and word variant recognition, acronym and abbreviation disambiguation, or document segmentation on the plurality of textual components,
      (b) analyzing the computer readable text to derive a textual component of the plurality of textual components,
      (c) identifying two or more medical findings from the derived textual component, wherein an electronic knowledge base is used to identify the two or more medical findings from the derived textual component, (d) determining a context for each of the two or more medical findings, wherein each context comprises one or more modifiers or attributes for the corresponding medical finding and wherein determining the context for each of the two or more medical findings comprises determining one or more relationships between the two or more medical findings and associated anatomical regions, and (e) outputting the dataset, wherein the dataset comprises each of the two or more medical findings and their respective corresponding contexts; and performing, by the incidental finding circuitry, incidental medical finding processing, wherein the incidental medical finding processing comprises:

(a) receiving, by the incidental finding circuitry, the dataset comprising each of the two or more medical findings and their respective corresponding contexts output by the natural language processing circuitry, (b) identifying, by the incidental finding circuitry, an excluded set of the two or more medical findings to exclude from further processing based at least in part on their respective corresponding contexts, (c) identifying, by the incidental finding circuitry, an included set of the two or more medical findings to include for further processing based at least in part on their respective corresponding contexts, wherein the included set of the two or more medical findings comprises two or more incidental medical findings, (d) querying, by the incidental finding circuitry, a database for one or more properties or one or more rules for identifying clinical cues associated with at least one of the two or more incidental medical findings of the included set of the two or more medical findings, for an associated condition of concern, (e) identifying, by the incidental finding circuitry and based at least in part on the one or more properties or the one or more rules returned from the query, one or more clinical cues for each incidental medical finding of the two or more incidental medical findings of the included set of the two or more medical findings, (f) determining, by the incidental finding circuitry and based at least in part on their respective corresponding contexts of the included set of the two or more medical findings, a gradient severity score for each of the one or more clinical cues, and (g) determining, by the incidental finding circuitry and based at least in part on the respective gradient severity scores, a gradient risk level for a condition of concern corresponding to the one or more clinical cues, wherein (1) determining the gradient risk level for the condition of concern corresponding to the one or more clinical cues is in combination with one or more predefined risk levels, (2) a predefined risk level of the one or more predefined risk levels for the condition of concern is a medium risk level, and (3) the gradient risk level is adjusted based at least in part on the context of the clinical cues;

responsive to determining that the gradient risk level for the condition of concern corresponding to the one or more clinical cues satisfies one or more filter criteria, generating, by the circuitry, a condition alert indicating the condition of concern, wherein (1) the condition alert comprises at least one clinical cue satisfying at least one of the one or more filter criteria or the corresponding gradient severity score, and (2) generating the condition alert comprises at least one of (I) inserting a flag in an electronic medical record or (II) at least one of outputting an output indicator using a computer assisted coding application, providing a notification via a user interface, or outputting a medical report.

2. The computer-implemented method of claim 1, wherein determining the context of the two or more medical findings further comprises one or more of:

determining, by the circuitry, from the one or more relationships, one or more relation facts, wherein the one or more relation facts indicate that the corresponding medical finding is due to benign or less significant conditions;

determining, by the circuitry, a patient history for one or more of the two or more incidental medical findings;

determining, by the circuitry, a clinical impression for one or more of the two or more incidental medical findings;

determining, by the circuitry, a clinical change for one or more of the two or more incidental medical findings;

determining, by the circuitry, a clinical qualification for one or more of the two or more incidental medical findings;

determining, by the circuitry, a clinical quantification for one or more of the two or more incidental medical findings; or determining, by the circuitry, a clinical modifier for one or more of the two or more incidental medical findings, wherein the clinical modifier comprises at least characteristics which indicate the corresponding medical finding is not a significant incidental finding.

3. The computer-implemented method of claim 1, wherein the location in the textual component of the medical report from which the two or more medical findings were determined is traceable.

4. The computer-implemented method of claim 1, wherein the condition alert further comprises the context, qualifiers, quantifiers, and other factors for the at least one clinical cue.

5. The computer-implemented method of claim 1, wherein (a) generating the condition alert comprises providing the notification via the user interface and (b) the circuitry comprises the incidental finding circuitry.

6. The computer-implemented method of claim 1, wherein machine learning is used to determine gradient risk levels based at least in part on past gradient risk level determinations.

7. An apparatus for identifying a condition of concern based at least in part on two or more incidental medical findings, the apparatus configured to:

receive, by circuitry, a dataset output by natural language processing circuitry, wherein the natural language processing circuitry is configured to:

receive an electronic medical report, wherein the electronic medical report comprises a plurality of textual components and at least one non-textual component; and perform natural language processing, wherein the natural language processing comprises:

(a) processing the plurality of textual components of the electronic medical report from natural language text to computer readable text by performing at least one of text normalization, tokenization, paraphrase and word variant recognition, acronym and abbreviation disambiguation, or document segmentation on the plurality of textual components,
(b) analyzing the computer readable text to derive a textual component of the plurality of textual components,
(c) identifying two or more medical findings from the derived textual component, wherein an electronic knowledge base is used to identify the two or more medical findings from the derived textual component,
(d) determining a context for each of the two or more medical findings, wherein each context comprises one or more modifiers or attributes for the corresponding medical finding and wherein determining the context for each of the two or more medical findings comprises determining one or more relationships between the two or more medical findings and associated anatomical regions, and
(e) outputting the dataset, wherein the dataset comprises each of the two or more medical findings and their respective corresponding contexts; and perform, using incidental finding circuitry module, incidental medical finding processing, wherein the incidental medical finding processing comprises:
(a) receiving, using the incidental finding circuitry, the dataset comprising each of the two or more medical findings and the corresponding contexts output by the natural language processing circuitry,
(b) identifying, using the incidental finding circuitry, an excluded set of the two or more medical findings to exclude from further processing based at least in part on their respective corresponding
(c) identifying, using the incidental finding circuitry, an included set of the two or more medical findings to include for further processing based at least in part on their respective corresponding contexts, wherein the included set of the two or more medical findings comprises two or more incidental medical findings
(d) querying, using the incidental finding circuitry, a database for one or more properties or one or more rules for identifying clinical cues associated with at least one of the two or more incidental medical findings of the included set of the two or more medical findings, for an associated condition of concern,
(e) identifying, using the incidental finding circuitry and based at least in part on the one or more properties or the one or more rules returned from the query, one or more clinical cues for each incidental medical finding of the two or more incidental medical findings of the included set of the two or more medical findings,
(f) determining, using the incidental finding circuitry and based at least in part on their respective corresponding contexts of the included set of the two or more medical findings, a gradient severity score for each of the one or more clinical cues, and
(g) determining, using the incidental finding circuitry and based at least in part on the respective gradient severity scores, a gradient risk level for a condition of concern corresponding to the one or more clinical cues, wherein (1) determining the gradient risk level for the condition of concern corresponding to the one or more clinical cues is in combination with one or more predefined risk levels, (2) a predefined risk level of the one or more predefined risk levels for the condition of concern is a medium risk level, and (3) the gradient risk level is adjusted based at least in part on the context of the clinical cues,
responsive to determining that the gradient risk level for the condition of concern corresponding to the one or more clinical cues satisfies one or more filter criteria, generating a condition alert indicating the condition of concern, wherein (1) the condition alert comprises at least one clinical cue satisfying at least one of the one or more filter criteria or the corresponding gradient severity score, and (2) generating the condition alert comprises at least one of (I) inserting a flag in an electronic medical record or (II) at least one of outputting an output indicator using a computer assisted coding application, providing a notification via a user interface, or outputting a medical report.

8. The apparatus of claim 7, wherein the apparatus is further configured to:
determine, from the one or more relationships, one or more relation facts, wherein the one or more relation facts indicate that the corresponding medical finding is due to benign or less significant conditions;
determine a patient history for one or more of the two or more incidental medical findings;
determine a clinical impression for one or more of the two or more incidental medical findings;
determine a clinical change for one or more of the two or more incidental medical findings;
determine a clinical qualification for one or more of the two or more incidental medical findings;
determine a clinical quantification for one or more of the two or more incidental medical findings; or
determine a clinical modifier for one or more of the two or more incidental medical findings, wherein the clinical modifier comprises at least characteristics which indicate the corresponding medical finding is not an incidental finding.

9. The apparatus of claim 7, wherein the location in the textual component of the medical report from which the two or more medical findings were determined is traceable.

10. The apparatus of claim 7, wherein the condition alert further comprises the context, qualifiers, quantifiers, and other factors for the at least one clinical cue.

11. The apparatus of claim 7, wherein (a) generating the condition alert comprises providing the notification via the user interface and (b) the circuitry comprises the incidental finding circuitry.

12. The apparatus of claim 7, wherein machine learning is used to determine gradient risk levels based at least in part on past gradient risk level determinations.

13. A non-transitory computer-readable storage medium for identifying a condition of concern based at least in part on two or more incidental medical findings, the non-transitory computer-readable storage medium storing program code instructions that, when executed, cause a computing device to:
receive, by circuitry, a dataset output by natural language processing circuitry module, wherein the natural language processing circuitry is configured to:
receive an electronic medical report, wherein the electronic medical report comprises a plurality of textual components and at least one non-textual component; and perform natural language processing, wherein the natural language processing comprises:
  (a) processing the plurality of textual components of the electronic medical report from natural language text to computer readable text by performing at least one of text normalization, tokenization, paraphrase and word variant recognition, acronym and abbreviation disambiguation, or document segmentation on the plurality of textual components,
  (b) analyzing the computer readable text to derive a textual component of the plurality of textual components,
  (c) identifying two or more medical findings from the derived textual component, wherein an electronic knowledge base is used to identify the two or more medical findings from the derived textual component,
  (d) determining a context for each of the two or more medical findings, wherein each context comprises one or more modifiers or attributes for the corresponding medical finding and wherein determining the context for each of the two or more medical findings comprises determining one or more relationships between the two or more medical findings and associated anatomical regions, and
  (e) outputting the dataset, wherein the dataset comprises each of the two or more medical findings and their respective corresponding contexts; and perform, using incidental finding circuitry, incidental medical finding processing, wherein the incidental medical finding processing comprises:
  (a) receiving, using the incidental finding circuitry, the dataset comprising each of the two or more medical findings and the corresponding contexts output by the natural language processing circuitry,
  (b) identifying, using the incidental finding circuitry, an excluded set of the two or more medical findings to exclude from further processing based at least in part on their respective corresponding
  (c) identifying, using the incidental finding circuitry, an included set of the two or more medical findings to include for further processing based at least in part on their respective corresponding contexts, wherein the included set of the two or more medical findings comprises two or more incidental medical findings
  (d) querying, using the incidental finding circuitry, a database for one or more properties or one or more rules for identifying clinical cues associated with at least one of the two or more incidental medical findings of the included set of the two or more medical findings, for an associated condition of concern,
  (e) identifying, using the incidental finding circuitry and based at least in part on the one or more properties or the one or more rules returned from the query, one or more clinical cues for each incidental medical finding of the two or more incidental medical findings of the included set of the two or more medical findings,
  (f) determining, using the incidental finding circuitry and based at least in part on their respective corresponding contexts of the included set of the two or more medical findings, a gradient severity score for each of the one or more clinical cues, and
  (g) determining, using the incidental finding circuitry and based at least in part on the respective gradient severity scores, a gradient risk level for a condition of concern corresponding to the one or more clinical cues, wherein (1) determining the gradient risk level for the condition of concern corresponding to the one or more clinical cues is in combination with one or more predefined risk levels, (2) a predefined risk level of the one or more predefined risk levels for the condition of concern is a medium risk level, and (3) the gradient risk level is adjusted based at least in part on the context of the clinical cues;

responsive to determining that the gradient risk level for the condition of concern corresponding to the one or more clinical cues satisfies one or more filter criteria, generating a condition alert indicating the condition of concern, wherein (1) the condition alert comprises at least one clinical cue satisfying at least one of the one or more filter criteria or the corresponding gradient severity score, and (2) generating the condition alert comprises at least one of (I) inserting a flag in an electronic medical record or (II) at least one of outputting an output indicator using a computer assisted coding application, providing a notification via a user interface, or outputting a medical report.

14. The non-transitory computer-readable storage medium of claim 13, wherein the non-transitory computer-readable storage medium storing program code instructions that, when executed, cause the computing device to further:
  determine, from the one or more relationships, one or more relation facts, wherein the one or more relation facts indicate that the corresponding medical finding is due to benign or less significant conditions;
  determine a patient history for one or more of the two or more incidental medical findings;
  determine a clinical impression for one or more of the two or more incidental medical findings;
  determine a clinical change for one or more of the two or more incidental medical findings;
  determine a clinical qualification for one or more of the two or more incidental medical findings;
  determine a clinical quantification for one or more of the two or more incidental medical findings; or
  determine a clinical modifier for one or more of the two or more incidental medical findings, wherein the clinical modifier comprises at least characteristics which indicate the corresponding medical finding is not an incidental finding.

15. The non-transitory computer-readable storage medium of claim 13, wherein the condition alert further comprises the context, qualifiers, quantifiers, and other factors for the at least one clinical cue.

16. The non-transitory computer-readable storage medium of claim 13, wherein (a) generating the condition alert comprises providing the notification via the user interface and (b) the circuitry comprises the incidental finding circuitry.

17. The non-transitory computer-readable storage medium of claim 13, wherein machine learning is used to determine gradient risk levels based at least in part on past gradient risk level determinations.

* * * * *

UNITED STATES PATENT AND TRADEMARK OFFICE
CERTIFICATE OF CORRECTION

| | | |
|---|---|---|
| PATENT NO. | : 11,869,667 B2 | Page 1 of 1 |
| APPLICATION NO. | : 17/454497 | |
| DATED | : January 9, 2024 | |
| INVENTOR(S) | : Brian C. Potter et al. | |

It is certified that error appears in the above-identified patent and that said Letters Patent is hereby corrected as shown below:

In the Claims

In Column 23, Line 25, Claim 7, delete "circuitry module," and insert -- circuitry, --, therefor.

In Column 24, Line 62, Claim 13, delete "circuitry module," and insert -- circuitry, --, therefor.

Signed and Sealed this
Sixteenth Day of April, 2024

Katherine Kelly Vidal
*Director of the United States Patent and Trademark Office*